United States Patent [19]

Eisenberg et al.

[11] 4,071,412

[45] Jan. 31, 1978

[54] READY MADE STERILIZED CULTURE MEDIA AND PROCESS OF PREPARATION

[75] Inventors: Eli Eisenberg, Tel-Aviv; Gideon Altmann, Petah Tiqua; Bianca Bogokovsky, Tel-Hashomer; Mordechai Lapidot, Bne Braq, all of Israel

[73] Assignee: The State of Israel and Isorad Isotope and Radiation Enterprise, Ltd., Israel

[21] Appl. No.: 574,644

[22] Filed: May 5, 1975

[30] Foreign Application Priority Data

May 17, 1974 Israel ........................................ 44853

[51] Int. Cl.² ................................................ C12K 1/10
[52] U.S. Cl. ..................................... 195/102; 195/100
[58] Field of Search .......... 195/100, 101, 102, 103.5 R

[56] References Cited

U.S. PATENT DOCUMENTS

| 3,346,464 | 10/1967 | Ernst | 195/100 |
| 3,838,013 | 9/1974 | Bergeron | 195/103.5 R |

OTHER PUBLICATIONS

Difco Manual, 9th Ed. (1953), Difco Labs. Incorporated, Detroit 1, Michigan, pp. 93, 94, 131, 132, 166–168, 199–200, 268–269, and 278–282.

*Primary Examiner*—Alvin E. Tanenholtz
*Assistant Examiner*—C. A. Fan
*Attorney, Agent, or Firm*—Weingarten, Maxham & Schurgin

[57] ABSTRACT

A process for preparing sterile culture media in unit dosage form which comprises preparing a composition of such media of conventional composition, adjusted or augmented by adding constituents in such manner that after sterilization by ionizing radiation a sterile medium of satisfactory composition is obtained. Additional constituents added are radio protectors, increased quantities of indicators, enzymes preventing the formation of toxic degradation products, vitamins or a combination of any of these.

10 Claims, No Drawings

READY MADE STERILIZED CULTURE MEDIA AND PROCESS OF PREPARATION

BACKGROUND OF THE INVENTION

The present invention relates to sterile culture media and to a novel process for the production of same. More particularly, the invention relates to sterile, liquid or solid, culture media in unit dosage form and to their production. Other and further features of the present invention will become apparent hereinafter.

The sterilization according to the present invention is effected by means of ionizing radiation. This is done by means of first preparing the culture medium, filling a desired quantity into a suitable container and sterilizing the packaged medium by means of ionizing radiation of suitable intensity and duration.

It is preferred to effect the sterilization with gamma radiation. It is also possible to use other types of ionizing radiation, such as X-rays and electron beams of suitable intensity. Care must be taken not to use such radiations which bring about the formation of radioactive products.

STATE OF THE PRIOR ART

The sterilization of various products by means of gamma radiation is well known and widely used. Hitherto various attempts were made to examine the effect of gamma radiation on culture media, and in most cases deleterious effects were observed. The result was generally that the capability of such irradiated media to support the growth of bacteria was seriously impaired, and this in comparison with heatsterilized culture media of equal initial composition. The effect of gamma radiation on culture media was examined amongst others by:

a. H. E. Frey et al, Radiation Research, 28, 663–672 (1966);
b. H. E. Frey et al, Radiation Research, 36, 59 – 67 (1968);
c. V. L. Chopea, Mutation Res. 8, 25–33 (1969);
d. I. H. Blank et al., J. Bac. 30, 21–32 (1935);
e. E. C. Pollard et al., Radiation Res. Supp.6, 194–200 (1966);
f. J. H. Becking, Misc. Papers, 9 (1971) Landbouwhogschool Wageningen, Netherlands;
g. P. C. Kesawan, Radiation Botany 11, 253–281 (1971).

In view of the above it was generally assumed that gamma radiation cannot be effectively used for the sterilization of packaged culture media. The deleterious effects of such radiation is generally due to the formation of certain decomposition products and also due to the decrease of the concentration of certain necessary ingredients of the culture medium. In some cases toxic products are formed and these impair or even prevent the growth of microorganisms. Redox potentials are changed and certain indicators commonly used are destroyed by such irradiation.

DESCRIPTION OF THE PRESENT INVENTION

The present invention relates to a process for preparing sterile culture media in unit dosage form which comprises preparing a composition of such media of conventional composition, adjusted or augmented by adding constituents in such manner that after sterilization by ionizing radiation a sterile medium of satisfactory composition is obtained. Additional constituents added are radio protectors, increased quantities of indicators, enzymes preventing the formation of toxic degradation products, vitamins or a combination of any of these.

In spite of the generally accepted assumption that such irradiation cannot be effectively used for the intended sterilization, the above drawbacks are overcome by the process of the present invention. The process is applicable to culture media which can be broadly grouped into "solid" and "liquid" ones. Culture media can be grouped according to the characteristic constituents of same. The drawbacks of gamma irradiated culture media are eliminated according to the present invention by certain adjustments of the initial composition of said culture media, the nature of the adjustment depending on the composition of the medium. For example, the destruction of certain critical components is prevented by the addition of adequate quantities of radio protectors. Certain constituents, such as vitamins or indicators are augmented so as to retain an adequate concentration after irradiation. The formation of certain toxic products is prevented by adding enzymes like catalase. Certain indicators are maintained at an efficient level by the addition of radio protectors and/or by starting with a higher initial concentration compared with that of conventional culture media.

Sterilized culture media were prepared according to the present invention and tested with a wide variety of microorganisms. Satisfactory results, as compared with conventionally sterilized media, were obtained.

The process according to the present invention for the manufacture of culture media in unit dosage form comprises essentially preparing a suitable culture medium, adjusted initially, if necessary, by the addition of certain additives to remain suitable after sterilization for the intended use, filling the medium into suitable containers and sterilizing same by means of ionizing radiation. The sterilization is advantageously effected at a dose of about 0.5 to 2.5 Mrad. The equipment for effecting the sterilization according to the invention is comparatively simple and only one process step of sterilization is needed. Furthermore, the manipulation of sterile materials is obviated.

DESCRIPTION OF PREFERRED EMBODIMENTS

Further features of the invention will become apparent from the following description, which is intended to serve as illustration of the invention and which is to be construed in a non-limitative manner.

EXAMPLE 1

Triple Sugar Iron Agar

A mixture of conventional composition was prepared, with the modification that the phenol red content was increased to 60 mg per liter, as part of the phenol red is decomposed during irradiation. 65 g. dry culture medium were boiled in 1000 ml of water, cooled to 60° C, poured into tubes to obtain the necessary slant and butt. After cooling and formation of the gel, the tubes were stoppered and sterilized by gamma radiation of 1.0 Mrad. The thus obtained culture medium was sterile, it was stored for a number of weeks and tested after sterilization and after storage. This culture medium was tested as to performance with the following bacteria: *Salmonella typhi; Salmonella typhimurium; Salmonella enteritidis; Salmonella haifa* and other serotypes belonging to Salmonella groups C, G + E, *Shigella flexneri* 2,

*Shigella flexneri* 4, *Shigella flexneri* 5, *Shigella flexneri* 6, *Shigella sonnei, Pseudomonas aeruginoss, Pasteurella pseudo-tuberculosis, Vibris cholerae* biotype El Tor, *E.-Coli* OSS, *Proteus morgani; Proteus vulgaris, Proteus rettgeri,* Providence, Citrobacter, Serratia, *E.hafniae* and *E. cloacae*. In all cases identical growth as with conventionally sterilized similar culture media were obtained.

Similar results were obtained by X-ray irradiation of similar dosage.

EXAMPLE 2

Mueller Hinton Agar

A conventional composition was prepared, with the modification of the increase of the agar content by 25 percent. Catalase was added to contain 10 keil units per liter. The addition and change of concentration of these was made so as to obtain the desired gel strength and to eliminate toxic effects due to gamma irradiation. A quantity of 38 g. of this composition (including added agar) was boiled in 1000 ml distilled water and after cooling to 50° C the catalase was added, plates were poured and these were packed into polyethylene sleeves which were hermetically closed.

The sealed sleeves containing the agar plates were sterilized at a dose of 1-2 Mrad. The sterilized plates were stored for 6 weeks and tested both after sterilization and storage.

The microorganisms tested were: *Streptococcus faecalis; N. Meningitidis; Pasteurella pseudo-tuberculosis, Salmonella typhi; Salmonella typhimurium; Shigella boydii, Staphylococcus aureus; Shigella flexneri;* Serratia; *Vitro cholerae* biotype El Tor; Klebsiella; Proteus; *E.Coli* 055; *Pseudomonas seruginosa*. With all strains satisfactory growth was obtained on this medium.

EXAMPLE 3

Fluid Thioglycollate Medium

A conventional composition was modified by an increase of the initial thioglycollate content to 1.5 g. per liter, This modification is necessary so as to maintain the redox potential necessary for the growth of anaerobic bacteria. 29.5 g. of the composition were boiled in 1000 ml distilled water, cooled to 60° C. and poured into plastic tubes. These were stoppered and sterilized by means of gamma radiation of 1-2 Mrad. After sterilization and after storage for 6 weeks, the culture media was tested and found to be suitable for bacteriological work.

*Clostridium perfringens, Strep/hemolyticus* group A; *Strep. faecallis, Strep/viridans* and *E. coli* were innoculated and satisfactory growth was obtained even with small inocular.

EXAMPLE 4

Fluid Thioglycollate Medium

A medium was prepared as in Example 3, but there was used the regular thiglycollate content to which there was added 1.00 g. cysteine per liter. Similar results were obtained.

EXAMPLE 5

Brian Heart Infusion 37 g. of culture medium were boiled in 1000 ml. distilled water, cooled to 60° C. poured into plastic tubes and stoppered. After gamma sterilization at 2.0 Mrad. the sterile liquid culture medium was stored for 6 weeks and tested after preparation and after storage. It was found to be suitable for all conventional bacteriological work. *Streptococcus viridans; Strep. hemolyticus, Strep. faecalis; Salmonella typhimurium; E.Coli; Staph. aureus* were grown on the thus prepared medium and growth was entirely satisfactory.

EXAMPLE 6

Tryptose Agar 41 g. of tryptose agar were boiled in 1000 ml distilled water, cooled to 60° C. plates were poured and sealed in polyethylene sleeves. After gamma irradiation at a does of 1.0 to 2.0 Mrad. the sterile culture medium was stored for 6 weeks and tested. It was found to be suitable for all conventional purposes.

The following bacteria were grown on this agar and growth was found to be satisfactory: *N.meningitidis; Brucella melitensis; E. coli, Shigella boydii; Staphylococcus aureus; Streptococcus faecalis.*

EXAMPLE 7

Agar MacConkey

The conventional formulation was increased to 70 mg neutral red per liter and thioglycollate or cysteine was added at a quantity of 0.01 M per liter. 50 g. of the medium were dissolved in 1000 ml distilled water, poured into petri dishes, packed in polyethylene sleeves and sterilized with gamma rays at 0.5-2.0 Mrad. After sterilization and after storage of 4 weeks the medium was tested and found to be suitable for the cultivation of gram negative bacilli.

Klebsiella, Herrelea; Serratia, Proteus, Levinea, *Pseudomonas aeruginosa; E.coli, Shigella boydii* and *Salmonella typhimurium* were grown and growth was up to standard.

EXAMPLE 8

C.L.E.D.

The conventional formula was modified by an increase of the brom-thymol blue content to 40 mg per liter and by adding 0.01 M thioglycollate or crystamine per liter. 36.2 g. were dissolved in 1000 ml boiling water, cooled to 50° C. and poured into plastic petri dishes and sealed in polyethylene sleeves. After sterilization with gamma rays at 1-2 Mrad. The medium was stored for 6 weeks and tested after sterilization and after storage. It was found to be suitable for all types of bacteriological work.

The following bacteria were innoculated and found to yield good growth on this medium: Proteus; Levinea; *Pseudomonas aeruginosa; E.coli; Salmonella typhimurium;* Klebsiella, Herrellea, Serratia, *Shigella boydii, Staph. aureus, Strep, faecalis* and Candida.

EXAMPLE 9

Slide Kit

A dip slide kit was prepared, according to Guttmann et al., Brit.Med. J.iii, 343-345 (1967), and the two sides of the plastic slide were coated with C.L.E.D. and with MacConkey agar, respectively. The slide was inserted into a tight, hermetically closed plastic container and this was sterilized by gamma irradiation of 2 Mrad. The culture media was tested immediately after sterilization and a number of each containers were stored for 8 weeks. Satisfactory growth was obtained on both media.

Most of the Examples were repeated and instead of gamma rays there were used X-rays or irradiation by electrons, of similar dosage. Similar results were obtained.

What is claimed is:

1. A process for preparing sterile culture media in unit dosage form comprising the steps of:
   preparing culture media compositions of several different conventional constitutions, at least some of said culture media including an indicator in their conventional constitutions;
   adjusting said compositions by selectively adding radio protectors, enzymes adapted to pevent formation of toxic degradation products upon said media being subjected to ionizing irradiation, or additional quantities of indicator, said indicator being added only to those compositions of said conventional constitutions normally including an indicator; and
   sterilizing the culture media by means of ionizing irradiation, the amount of said added constituents being such that after said sterilization step of each of said compositions a sterile culture medium of quality sufficient to produce satisfactory bacterial growth as compared to non ionizing radiation sterilized medium is obtained.

2. A process for preparing a sterile culture medium in unit dosage form comprising the steps of:
   preparing a culture medium composition of conventional constitution containing a conventional amount of indicator;
   adding a further quantity of indicator of at least 50% above the conventional content thereof; then
   putting a desired quantity of said culture medium into a container; and then
   sterilizing said culture medium by means of ionizing irradiation, thereby obtaining a sterile culture medium of quality sufficient to produce satisfactory bacterial growth as compared to non ionizing radiation sterilized medium.

3. A process for preparing a sterile culture medium in unit dosage form comprising the steps of:
   preparing a culture medium composition of conventional constitution; then
   adding a radio protector; and then
   sterilizing said culture medium by means of ionizing irradiation, thereby obtaining a sterile culture medium of quality sufficient to produce satisfactory bacterial growth as compared to non ionizing radiation sterilized medium.

4. A process for preparing a sterile culture medium in unit dosage form comprising the steps of:
   preparing a culture medium composition of conventional constitution; then
   adding an enzyme adapted to prevent formation of toxic degradation products upon said medium being subjected to ionizing irradiation; and then
   sterilizing said culture medium by means of ionizing irradiation, thereby obtaining a sterile culture medium of quality sufficient to produce satisfactory bacterial growth as compared to non ionizing radiation sterilized medium.

5. The process according to claim 1 wherein said media composition is triple sugar iron agar, wherein said adjusting step comprises increasing the content of phenol red prior to sterilization, the percentage of phenol red in said composition being increased by at least 50% as compared with conventional formulations of said composition.

6. The process according to claim 1 wherein said media composition is Mueller Hinton agar, wherein said adjusting step comprises adding catalase prior to sterilization.

7. The process according to claim 1 wherein said media composition is fluid thioglycollate medium, wherein said ajdusting step comprises increasing the percentage of thioglycollate content in said composition prior to sterilization by at least 100%.

8. The process according to claim 1 wherein said media composition is fluid thioglycollate medium, wherein said adjusting step comprises adding cysteine prior to sterilization.

9. The process according to claim 1 wherein said media composition is MacConkey agar, wherein said adjusting step comprises increasing the percentage of the neutral red content in said composition by at least 50% and adding cysteine prior to sterilization.

10. The process according to claim 1 wherein said media composition is C.L.E.D. medium, wherein said adjusting step comprises increasing the percentage of the brom-thymol content in said composition by at least 50% and adding cysteamine prior to sterilization.

* * * * *